United States Patent
Barner et al.

Patent Number: 5,232,852
Date of Patent: Aug. 3, 1993

[54] PROCESS FOR THE PRODUCTION OF DIOXOLANES

[75] Inventors: Richard Barner, Witterswil; Josepf Hübscher, Nunningen; Beat Wirz, Reinach, all of Switzerland

[73] Assignee: Hoffmann-La Roche Inc., Nutley, N.J.

[21] Appl. No.: 492,166

[22] Filed: Mar. 13, 1990

[30] Foreign Application Priority Data

Mar. 23, 1989 [CH] Switzerland .................. 1093/89

[51] Int. Cl.$^5$ .................. C12P 7/62; C12P 17/02; C12N 9/16; C12N 9/18
[52] U.S. Cl. .................. 435/280; 435/123; 435/196; 435/197
[58] Field of Search .................. 351/280, 123, 196, 197

[56] References Cited

U.S. PATENT DOCUMENTS

| | | | |
|---|---|---|---|
| 4,629,701 | 12/1986 | Sakimae | 435/130 |
| 4,808,736 | 2/1989 | Barner et al. | 549/408 |
| 4,851,585 | 7/1989 | Barner et al. | 568/592 |

FOREIGN PATENT DOCUMENTS

| | | |
|---|---|---|
| 0244912 | 11/1987 | European Pat. Off. |
| 257503 | 3/1988 | European Pat. Off. |
| 269009 | 6/1988 | European Pat. Off. |

OTHER PUBLICATIONS

Sounet et al., *J. Agric Food Chem.*, 1988, vol. 36, pp. 856-862.
Wang et al., *J. Org. Chem.* vol. 53, 1988, pp. 3127-3129.
Pottie et al., *Tetrahedron Lett.*, 1989, vol. 30, pp. 5319-5322.
Fuganti et al., *J. Chem. Soc., Chem Commun*, 1987, pp. 538-539.
*J. Org. Chem.* (1983) 48, 3592-3594.
*J. Chem. Soc. Chem. Comm.* (1987) 538-539.
*J. Chem. Comm.* (1988) 1638-1639.
*J. Agric Food. Chem.*, (1988) 36, 856-862.
Fuganti, *Tetrahedron*, vol. 44, No. 9., pp. 2575 to 2582 (1988).
Holy, *Inst. of Org. Chem & Biochemistry*, vol. 54, pp. 248-265.

*Primary Examiner*—Irene Marx
*Attorney, Agent, or Firm*—George M. Gould; William H. Epstein

[57] ABSTRACT

Alcohols of the formula

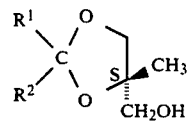

wherein $R^1$ and $R^2$ are each independently methyl or ethyl or together signify pentamethylene, formed by the enzymatic hydrolysis of a corresponding (RS) alkanoic acid ester are intermediates for Vitamin E.

2 Claims, No Drawings

PROCESS FOR THE PRODUCTION OF DIOXOLANES

SUMMARY OF THE INVENTION

The present invention is directed to a process for producing chiral dioxolane derivatives of the formula

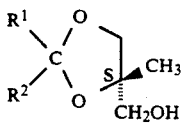

wherein $R^1$ and $R^2$ are each independently methyl or ethyl or taken together form pentamethylene,
and to a class of new dioxolane derivatives.

The compounds of formula Ib' and other members of the class of new dioxolane derivatives are valuable intermediates in the manufacture of vitamin E, especially of its optically active form d-α-tocopherol.

DETAILED DESCRIPTION

In accordance with this invention the compound of formula Ib' is produced by hydrolyzing a racemic alkanoic acid ester of the formula

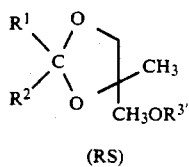

wherein $R^1$ and $R^2$ are as above, and $R^{3'}$ is alkanoyl containing from 2 to 9 carbon atoms;
through enzymatic hydrolysis using an enzyme of the sub-class carboxyl esterases (EC 3.1.1.1), triacylglycerol lipases (EC 3.1.1.3), cholesterol esterases (EC 3.1.1.13) or diacylglycerol lipases (EC 3.1.1.34). The so-produced alcohol of formula Ib' or the (S)-alkanoic acid ester of Ia, which is not reacted during the enzymatic hydrolysis in accordance with the invention, can be converted into d-α-tocopherol in a manner which will be explained in more detail hereinafter.

The hydrolysis is carried out in accordance with the invention under the influence of an enzyme of the above-mentioned sub-classes, preferably a lipase of microbial origin from *Pseudomonas fluorescens, Mucor miehei, Rhizopus delemar, Rhizopus arrhizus, Humicola lanuginosa, Rhizopus javanicus* or *Mucor javanicus*. Examples of suitable enzyme preparations are Lipase P-30 (*P. fluorescens*; Amano Pharmaceutical Co. Ltd., Nagoya, Japan), Lipase SAM (*P. fluorescens*; Amano; available under catalog No. 62312 from Fluka AG, Buchs, Switzerland), Lipase PM and LMM (*M. miehei*; Palatase M 1000L or Lipozyme IM 20; Novo Industri A/S, Bagsvaerd, Denmark), Lipase LRD and D (*R. delemar*; Seikagaku Kogyo Co. Ltd., Tokyo, Japan or Amano), Lipase LRA (*R. arrhizus*; Sigma Chemical Co., St. Louis, USA), Lipase CE (*H. lanuginosa*; Amano), Lipase FAP (*R. javanicus*; Amano) and Lipase MAP (*M. javanicus*; Amano).

The enzyme can be used not only in partially purified or completely pure form, but also in immobilized form.

The process in accordance with the invention is conveniently carried out in an organic/aqueous emulsion in which the organic phase can consist solely of the starting material of formula Ia, but which can optionally also contain a water-immiscible, non-polar or polar solvent such as, for example, n-hexane, isooctane or diethyl ether. One of the usual inorganic or organic buffers, e.g. sodium phosphate or sodium citrate, can be present in the aqueous phase, conveniently in a molar concentration of 1 mM to 1.0M, preferably 3 mM to 0.1M.

Moreover, the process in accordance with the invention can be carried out in the presence of a monohydric or polyhydric alcohol, e.g. ethanol or glycerol, conveniently at a molar concentration of 50 mM to 4M, preferably 50 mM to 0.5M; of calcium or magnesium ions; a commercial emulsifier, e.g. polyvinyl alcohol or Triton ® X-100; and/or a "salting-in" salt, e.g. lithium rhodanide or guanidinium chloride, conveniently at a molar concentration of 50 mM to 2M, preferably 50 mM to 0.5M.

The concentration of the substrate (alkanoic ester of formula Ia) in the total reaction medium is conveniently 0.5% to 50%, preferably 1% to 15%, with the percentage concentrations referring to weight/volume (w/v). The weight ratio enzyme:substrate conveniently amounts to 0.001–0.05:1.

The hydrolysis in accordance with the invention is conveniently effected at temperatures between 0° and 45° C., preferably between 10° and 35° C. The hydrolysis is conveniently carried out at a pH value of 6 to 9, preferably 7 to 8.

Starting from racemic (RS)-alkanoic ester Ia there is obtained initially as the reaction product predominantly the (S)-alcohol of formula Ib', i.e. the process in accordance with the invention is an asymmetric hydrolysis in that the (R)-ester of the racemic mixture Ia can hydrolyze to the (S)-alcohol Ib' under the influence of the enzyme much more rapidly than the (S)-ester can hydrolyze to the (R)-alcohol of the formula

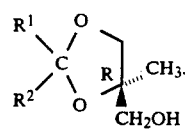

Thereby, at up to a 50 percent reaction conversion the by far predominant part of the (S)-ester, i.e. of the formula

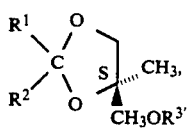

of the racemic mixture Ia remains behind. It has been found that at up to a 50 percent reaction conversion the ratio alcohol Ib' [(S)-alcohol]:alcohol Ib" [(R)-alcohol], i.e. the so-called ee value (enantiomeric excess or enantiomeric purity), remains extremely high, namely at at least 90%, in most cases at about 98%. Herein lies the advantage of the process in accordance with the invention. A further material advantage of the process in accordance with the invention is that with the formation of the product Ia' no mere byproduct arises, but rather a product (of formula Ia') which can also be converted into d-α-tocopherol.

After the 50 percent reaction conversion has been achieved, i.e. at the point in time when the conversion of the (R)-ester present in the racemate Ia to the (S)-alcohol Ib' has been completed (which can be established by conventional analytical methods, e.g. titration), the enzymatic hydrolysis reaction can be stopped by conventional means, for example by the addition of an organic solvent, e.g. methylene chloride or methyl tert.butyl ether. The (S)-alcohol and the unreacted (S)-ester are then isolated from the reaction mixture, e.g. by extraction with an organic solvent such as, for example, chloroform or methyl tert.butyl ether and subsequent evaporation of the solvent, and the two components are separated from one another, e.g. by fractional distillation or column chromatography.

As mentioned above, the compounds of formulae Ia' and Ib' are valuable intermediates in the manufacture of optically active d-α-tocopherol. The respective synthetic approaches which can be carried out using these intermediates are illustrated in the following Reaction Scheme:

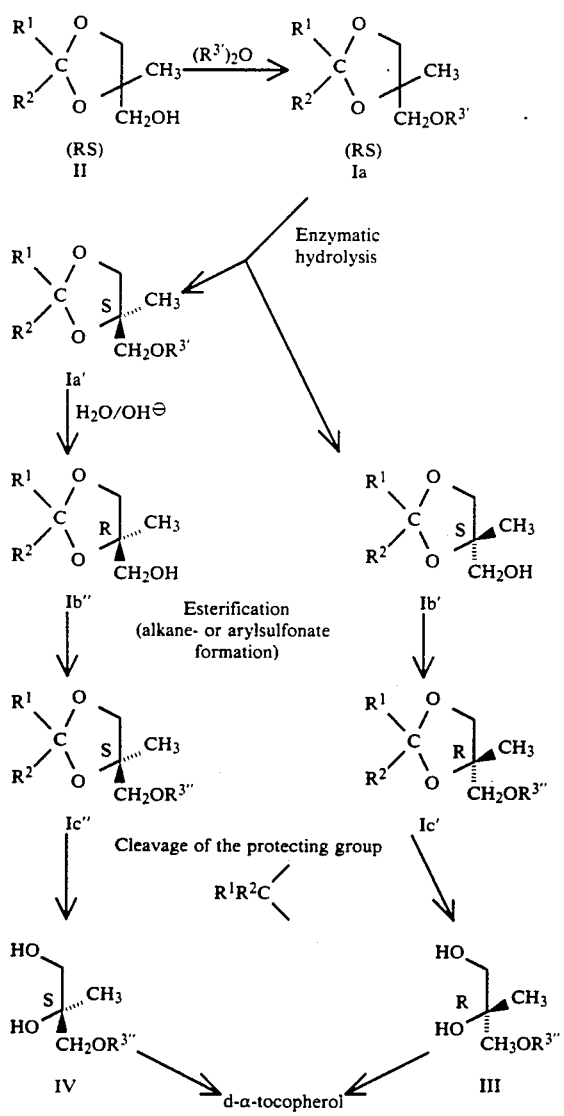

In the above Reaction Scheme $R^{3'}$ signifies $C_{2-9}$-alkanoyl, i.e. acetyl to nonanoyl, with n-butyryl being preferred; and $R^{3''}$ signifies alkanesulfonyl or arylsulfonyl, preferably methanesulfonyl (mesyl) or p-tolylsulfonyl (tosyl). The compounds of formulae II and Ia occur as racemates [(RS)-forms], while the compounds of formulae Ib'', Ic' and III are present in the (R)-enantiomeric form and the compounds of formulae Ia', Ib', Ic'' and IV are present in the (S)-enantiomeric form. In these formulae it is to be understood by the symbol ⫼⫼ or ◄ that the substituent $CH_3$, $CH_2OR^{3'}$, $CH_2OH$ or $CH_2OR^{3''}$ lies below and, respectively, above the plane of the molecule.

The (RS)-alcohols of the formula II, which are used as starting materials, are to some extent known (see e.g. J. Org. Chem. 1983, 45, 3592–3594, and J. Chem. Soc., Chem. Commun., 1987, 538–539, in which there are described those (RS)-compounds II in which not only $R^1$ but also $R^2$ signifies methyl). The remaining, i.e. novel, (RS)-alcohols of formula II, i.e. those compounds of formula II in which $R^1$ and $R^2$ have the significances given above although do not both signify methyl, can be produced according to methods known per se.

Most of the intermediates of formulae Ia, Ia', Ib', Ib'', Ic' and Ic'' are novel and form a further object of the present invention. These novel compounds are embraced by formula I hereinafter:

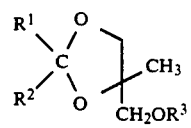

wherein $R^1$ and $R^2$ each independently signify methyl or ethyl or together signify pentamethylene and $R^3$ signifies hydrogen, $C_{2-9}$-alkanoyl, alkanesulfonyl or arylsulfonyl, with the provisos that $R^3$ is different from hydrogen where $R^1$ and $R^2$ both stand for methyl, and that the compound I is chiral where $R^1$ and $R^2$ together stand for pentamethylene and $R^3$ stands for hydrogen.

Under the compounds of formula I there are accordingly to be understood not only the chiral compounds [(R)- or (S)-enantiomeric form] but also mixtures of the two forms, i.e. the racemates, and {2-methyl-1,4-dioxaspiro[4,5]-dec-2-yl}methanol (formula I in which $R^1$ and $R^2$ together signify pentamethylene and $R^3$ signifies hydrogen) as the racemate is excluded.

From the definition of the compounds of formula I and the above Reaction Scheme it will be evident that the novel compounds of formula I in accordance with the invention consist of the following sub-classes:

The compounds of the formula Ia in which $R^1$ and $R^2$ have the significances given above and $R^{3'}$ signifies $C_{2-9}$-alkanoyl [among these compounds there are to be found especially the racemates [(RS)-form], which are the products of the reaction of the racemic compounds of formula II with the respective acid anhydride $(R^{3'})_2O$, as well as the compounds of formula Ia', i.e. the (S)-enantiomers];

The compounds of the formula

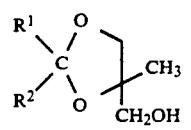

wherein $R^1$ and $R^2$ each independently signify methyl or ethyl or together signify pentamethylene, with the provisos that $R^1$ and $R^2$ do not both stand for methyl, and that the compound Ib is chiral where $R^1$ and $R^2$ together stand for pentamethylene, i.e. is present either in the (R)-enantiomeric form or in the (S)-enantiomeric form [among these compounds there are to be found especially compounds of formula Ib', i.e. the (S)-enantiomers, as well as compounds of formula Ib'', i.e. the (R)-enantiomers];

as well as the compounds of the formula

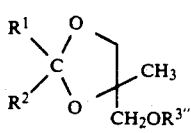

Ic wherein $R^1$ and $R^2$ each independently signify methyl or ethyl or together signify pentamethylene and $R^{3''}$ signifies alkanesulfonyl or arylsulfonyl, among which there are to be found especially the compounds of formula Ic', i.e. the (R)-enantiomers, as well as the compounds of formula Ic'', i.e. the (S)-enantiomers.

In accordance with the definition formulae Ib' and Ib'' embrace not only novel compounds, but also the known compounds of formulae Ib' and Ib'' in which $R^1$ and $R^2$ both stand for methyl (see J. Org. Chem. 1983, 48, 3592–3594 and J. Chem. Soc. Chem. Commun., 1987, 538–539).

Under the term "$C_{2-9}$-alkanoyl" there are to be understood not only straight-chain but also branched alkanoyl groups. This also applies to "alkanesulfonyl" ($R^{3''}$). with the alkane part being especially $C_{1-4}$-alkyl. The arylsulfonyl group ($R^{3''}$) is especially phenylsulfonyl, tolylsulfonyl or naphthylsulfonyl. As mentioned above, the preferred $C_{2-9}$-alkanoyl, alkanesulfonyl or arylsulfonyl group is, respectively, n-butyryl, methanesulfonyl (mesyl) or p-toluenesulfonyl (tosyl).

Especially preferred individual compounds in accordance with the invention are:

Formula Ia or Ia':
{(R,S)-2-Methyl-1,4-dioxaspiro[4,5]dec-2-yl}methyl butyrate,
{(R,S)-2,2,4-trimethyl-1,3-dioxolan-4-yl}methyl butyrate,
{(S)-2-methyl-1,4-dioxaspiro[4,5]dec-2-yl}methyl butyrate and
{(S)-2,2,4-trimethyl-1,3-dioxolan-4-yl}methyl butyrate.

Formula Ib' or Ib'':
{(S)-2-Methyl-1,4-dioxaspiro[4,5]dec-2-yl}methanol and
{(R)-2-methyl-1,4-dioxaspiro[4,5]dec-2-yl}methanol.

Formula Ic' or Ic'':
{(R)-2-Methyl-1,4-dioxaspiro[4,5]dec-2-yl}methyl tosylate,
{(R)-2,2,4-trimethyl-1,3-dioxolan-4-yl}methyl tosylate,
{(S)-2-methyl-1,4-dioxaspiro[4,5]dec-2-yl}methyl tosylate and
{(S)-2,2,4-trimethyl-1,3-dioxolan-4-yl}methyl tosylate.

Having regard to the carbon number of the basic structure the compounds I can be described as optically active $C_4$-building blocks.

The two products of the hydrolysis in accordance with the invention are the (S)-alcohol Ib' and the (S)-ester Ia', with the latter product being a (unreacted) component of the racemic starting material Ia. The known optically active diols of formulae III and IV can be produced from the two isolated products (see the Reaction Scheme). The one synthetic route is a conventional esterification of the (S)-alcohol Ib' to its alkanesulfonate or arylsulfonate of formula Ic', whereby the inversion S→R takes place, followed by a cleavage of the protecting group $R^1R^2C<$ which again is carried out under reaction conditions which are familiar to a person skilled in the art. In the case of the second synthetic route, the (S)-ester Ia' must firstly be hydrolyzed to the (R)-alcohol Ib'', which can be effected under reaction conditions which are familiar to the person skilled in the art. Thereafter, the (R)-alcohol can be converted into the diol of formula IV by esterification and subsequent cleavage of the protecting group $R^1R^2C<$, namely analogously to reaction steps Ib'→Ic' and Ic'→III. Thus, the esterification (Ib'→Ic' or Ib''→Ic'') is conveniently effected in an inert organic solvent, preferably a halogenated aliphatic hydrocarbon, especially methylene chloride, at temperatures between 0° C. and room temperature. The alkanesulfonating or arylsulfonylating agent is suitably the corresponding sulfonic acid chloride such as, for example, methanesulfonyl chloride (mesyl chloride) or p-toluenesulfonyl chloride (tosyl chloride). Moreover, the presence of a base such as a tertiary amine, preferably triethylamine, is advantageous. The subsequent cleavage of the protecting group (Ic'→III or Ic''→IV) is also conveniently carried out in an inert organic solvent, preferably in a lower alcohol such as a methanol. Moreover, the reaction is suitably effected in the presence of a catalytic amount of a sulfonic acid such as p-toluenesulfonic acid. A preferred method comprises subjecting the protected compound (Ic' or Ic'') to a trans-ketalization. For example, a 1,4-dioxaspiro[4,5]decane derivative of formula Ic' or Ic'' ($R^1$ and $R^2$ together signify pentamethylene) is repeatedly evaporated from methanol in the presence of p-toluene-sulfonic acid, whereby the diol product III or IV finally results.

The diols of formulae III and IV are known compounds (see, for example, European Patent Publications Nos. 257 503 and 269 009) and can be converted into d-α-tocopherol according to methods known per se (see, for example, the two above-mentioned European Patent Publications as well as European Patent Publication No. 129 252). The conversion of the S-diol (formula IV) into d-α-tocopherol can be effected by coupling this diol with the aromatic ring, subjecting the product to a ring closure and subsequently attaching the $C_{15}$-side chain or by carrying out the latter two reaction steps in reverse sequence. On the other hand, when using the R-diol (formula III), this is firstly coupled with the $C_{15}$-side chain in order to obtain the "$C_{19}$-building block". This is then linked benzylically with the aromatic ring and the ring closure is carried out. The details for the various reaction steps are to be found in the above-mentioned Patent Publications.

The conversion in accordance with the invention into d-α-tocopherol is carried out either by esterifying the alcohol of formula Ib', which is manufactured by the hydrolysis in accordance with the invention, to the corresponding (R)-alkanesulfonate or (R)-arylsulfonate of formula Ic', cleaving off the protecting group $R^1R^2C<$ and converting the resulting (R)-diol of formula III into d-α-tocopherol in a manner known per se or by hydrolyzing the (S)-alkanoic acid ester of formula Ia', which remains in the starting material during the enzymatic hydrolysis in accordance with the invention, to the corresponding (R)-alcohol of formula Ib", esterifying this (R)-alcohol to the corresponding (S)-alkanesulfonate or (S)-arylsulfonate of formula Ic", cleaving off the protecting group $R^1R^2C<$ and converting the resulting (S)-diol of formula IV into d-α-tocopherol in a manner known per se.

The following Examples illustrate the invention.

EXAMPLE 1

Production of {(R,S)-2-methyl-1,4-dioxaspiro[4,5]dec-2-yl}methyl butyrate 5.62 g (26.7 mmol) of (R,S)-2-methyl-1,4-dioxaspiro-[4,5]decane-2-methanol are dissolved in 20 ml of methylene chloride. 4.57 ml (3.32 g, 32.8 mmol) of triethylamine, 4.90 ml (4.75 g, 30.0 mmol) of butyric anhydride and a catalytic amount of 4-dimethylaminopyridine are added to the solution while stirring and the reaction mixture is subsequently stirred at room temperature for a further 5 hours. The mixture is then washed with water, the organic phase is concentrated under reduced pressure and the residue is purified by chromatography over silica gel 60 (0.040-0.063 mm, 300 g) using n-hexane/ethyl acetate (4:1) as the eluent. In this manner there are obtained 6.40 g (25.0 mmol, 93.5% of the theoretical yield) of the butyrate as a colourless oil which by gas chromatography is found to be more than 99% pure and which contains no traces of educt alcohol.

EXAMPLE 2

Production of {(R,S)-2,2,4-trimethyl-1,3-dioxolan-4-yl}methyl butyrate 17.3 g (118.3 mmol) of {(R,S)-2,2,4-trimethyl-1,3-dioxolan-4-yl}methanol are dissolved in 70 ml of methylene chloride. 23.0 ml (16.7 g, 165.0 mmol) of triethylamine, 19.4 ml (18.8 g, 118.7 mmol) of butyric anhydride and a catalytic amount of 4-dimethylaminopyridine are added to the solution while stirring and the reaction mixture is subsequently stirred at room temperature for a further 5 hours. The mixture is then washed with water, the organic phase is concentrated under reduced pressure and the residue is purified by chromatography over silica gel 60 (0.040-0.063 mm) using n-hexane/ethyl acetate (3:1) as the eluent. In this manner there are obtained 23.5 g (108.6 mmol, 91.8% of the theoretical yield) of the butyrate as a colourless oil which by gas chromatography is found to be more than 99% pure and which contains no traces of educt alcohol.

EXAMPLE 3

Manufacture of {(S)-2-methyl-1,4-dioxaspiro[4,5]dec-2-yl}methanol (asymmetric hydrolysis of {(R,S)-2-methyl-1,4-dioxaspiro[4,5]dec-2-yl}methyl butyrate)

100 mg (390 μmol) of {(RS)-2-methyl-1,4-dioxaspiro[4,5]dec-2-yl}methyl butyrate are emulsified in 25 ml of 0.1M sodium chloride solution and 1 ml of 0.1M sodium phosphate buffer at pH 7. After adjusting the pH value to 7.5 (or 7.0) with 0.1N sodium hydroxide solution the reaction is initiated by adding a catalytic amount of the respective enzyme. The pH value is held constant at 7.5 or 7.0 by stirring in 0.1N sodium hydroxide solution up to about 50 percent reaction conversion [after the addition of about 195 μmol of NaOH (50% ester equivalents, 1.95 ml)]. Thereafter, the reaction is interrupted by the addition of 25 ml of methylene chloride. The reaction mixture is extracted with 25 ml of methylene chloride, the phase separation being accelerated by centrifugation for a short time, the organic phase is dried over anhydrous magnesium sulfate, the solvent is evaporated off and the residue is subjected to capillary gas chromatography for the direct determination of the enantiomeric purity of the alcohol product (by means of chiral phase: permethylated β-cyclodextrin).

The enzymes used, the percentage conversion, the corresponding reaction time as well as the percentage enantiomeric purity (ee) of the thus-produced {(S)-2-methyl-1,4-dioxaspiro[4,5]dec-2-yl}methanol are given in Table 1 hereinafter.

TABLE 1

| Enzyme (amount used)* | Percentage conversion/ reaction time | Percentage ee of the alcohol product |
| --- | --- | --- |
| Lipase P-30 (200 U) | 48.6/35 min. | 99 |
| Lipase SAM (85 U) | 48.1/168 min.** | 99 |
| Lipase PM [Palatase M 1000 L] (100 μl) | about 50/40 min. | 98 |
| Lipase LMM [Lipozym IM 20] | about 49 | 91 |
| Lipase LRD (525 U) | 48.8/52 min. | 98 |
| Lipase D-20 (14 mg) | 49.2/38 min. | 97 |
| Lipase LRA (1481 U) | 49.5/15 min. | 97 |
| Lipase CE-5 (23 mg) | 49.0/10 min. | 98 |
| Lipase F-AP 15 (1008 U) | 47.6/176 min.** | 95 |
| Lipase M-AP 10 (80 U) | 48.7/168 min. | 96 |

*Amount in mg, μl or U (amount of units used according to details declared by the supplier)
**Reaction carried out at pH 7.0 (otherwise 7.5)

EXAMPLE 4

Manufacture of {(S)-2-methyl-1,4-dioxaspiro[4,5]dec-2-yl}methanol (asymmetric hydrolysis of {(R,S)-2-methyl-1,4-dioxaspiro[4,5]dec-2-yl}methyl butyrate, alternative method)

The procedure of Example 3 is repeated with the differences that 1.0 g (3.91 mmol) or 3.0 g (11.73 mmol) of the butyrate are used instead of 100 mg (390 μmol), and 1.0N sodium hydroxide solution is used instead of 0.1N sodium hydroxide solution as the titrating agent.

The respective details are set forth in Table 2 hereinafter:

TABLE 2

| Enzyme (amount used)*** | Amount of butyrate used | Percentage conversion/ reaction time | Percentage ee of the alcohol product |
| --- | --- | --- | --- |
| Lipase P-30 (600 U) | 1.0 g | 47.3/150 min. | 99.2 |
| Lipase P-30 (1800 U) | 3.0 g | 48.9/200 min. | 99.1 |
| Lipase PM [Palatase M 1000 L] (300 μl) | 1.0 g | 45.1/154 min. | 97.3 |
| Lipase PM [Palatase M 1000 L] (1.0 ml) | 3.0 g | 47.2 316 min. | 96.0 |

TABLE 2-continued

| Enzyme (amount used)*** | Amount of butyrate used | Percentage conversion/ reaction time | Percentage ee of the alcohol product |
| --- | --- | --- | --- |
| Lipase LRD (1575 U) | 1.0 g | 49.8/184 min. | 97.7 |
| Lipase LRD (5250 U) | 3.0 g | 48.6/370 min. | 95.9 |

***Amount in ml, μl or U (amount of units used according to details declared by the supplier)

EXAMPLE 5

Manufacture of
{(S)-2-methyl-1,4-dioxaspiro[4,5]dec-2-yl}methanol
(asymmetric hydrolysis of
{(R,S)-2-methyl-1,4-dioxaspiro[4,5]dec-2-yl}methyl butyrate)

The procedure of Example 3 is repeated using Lipase P-30 (200 U) at pH 7.5, but with the difference that 0.1M lithium rhodanide is used in place of 0.1M sodium chloride (variant A), 0.1M glycerol is used in place of 0.1M sodium chloride (variant B), 0.1M calcium chloride is used in place of 0.1M sodium chloride (variant C), 0.1M magnesium chloride is used in place of 0.1M sodium chloride (variant D) or the aqueous phase additionally contains 26 μl of Triton X-100 (variant E).

The respective details are set forth in Table 3 hereinafter:

| Variant | Percentage conversion | Reaction time | Percentage ee of the alcohol product |
| --- | --- | --- | --- |
| A | 49.5 | 41 min. | 99 |
| B | 49.6 | 48 min. | 99 |
| C | 49.5 | 36 min. | 99 |
| D | 49.6 | 29 min. | 99 |
| E | 49.5 | 59 min. | 99 |

EXAMPLE 6

Manufacture of
{(S)-2,2,4-trimethyl-1,3-dioxolan-4-yl}methanol
(asymmetric hydrolysis of
{(R,S)-2,2,4-trimethyl-1,3-dioxolan-4-yl}methyl butyrate)

100 mg (462 μmol) of {(R,S)-2,2,4-trimethyl-1,3-dioxolan-4-yl}methyl butyrate are hydrolyzed to the corresponding methanol derivative analogously to the procedure described in Example 3. For the determination of the enantiomeric purity of the alcohol product by capillary gas chromatography (permethylated β-cyclodextrin) it is previously converted into the corresponding benzoate using benzoyl chloride.

The enzymes used, the percentage conversion, the corresponding reaction time as well as the percentage enantiomeric purity (ee) of the thus-manufactured {(S)-2,2,4-trimethyl-1,3-dioxolan-4-yl}methanol are given in Table 4 hereinafter:

TABLE 4

| Enzyme (amount used)* | Percentage conversion/ reaction time | Percentage ee of the alcohol product |
| --- | --- | --- |
| Lipase P-30 (200 U) | 49.5/26 min. | 99.6 |
| Lipase SAM (85 U) | 49.5/81 min. | 99.6 |
| Lipase PM [Palatase M 1000 L] (100 μl) | 49.6/26 min. | 99.4 |
| Lipase LRD (525 U) | 49.5/28 min. | 98.2 |
| Lipase D-20 (14 mg) | 49.5/24 min. | 97.0 |
| Lipase F-AP 15 (1008 U) | 49.5/16 min. | 97.1 |
| Lipase M-AP 10 (80 U) | 49.5/60 min. | 96.6 |

*Amount of mg, μl or U (amount of units used according to details declared by the supplier)

EXAMPLE 7

Manufacture of
{(S)-2-methyl-1,4-dioxaspiro[4,5]dec-2-yl}methanol
(asymmetric hydrolysis of
{(R,S)-2-methyl-1,4-dioxaspiro[4,5]dec-2-yl}methyl butyrate)

5.00 g (19.5 mmol) of {(R,S)-2-methyl-1,4-dioxaspiro[4,5]dec-2-yl}methyl butyrate are emulsified in 100 ml of 0.1M sodium chloride solution and 4 ml of 0.1M sodium phosphate solution at pH 7 (concentration of butyrate about 4.6% w/v). The reaction is initiated by the addition of 74.0 mg of Lipase P-30. The pH value is held constant at 7.0 by stirring in 1.0N sodium hydroxide solution up to 45.6 percent reaction conversion (reaction time about 2.25 hours, addition of 8.90 ml of sodium hydroxide solution). Thereafter, the reaction is interrupted by the addition of 50 ml of methylene chloride. The reaction mixture is extracted twice with 50 ml of methylene chloride each time, the phase separation being accelerated by centrifugation for a short time, the combined organic phases are dried over anhydrous magnesium sulfate and the solvent is evaporated off at 16 mmHg/room temperature. This gives 4.44 g of a colorless oil which is purified by chromatography over silica gel 60 (0.040–0.063 mm, 99 g) using 500 ml of methylene chloride followed by 500 ml of methylene chloride/diethyl ether (1:1) as the eluent. In this manner there are obtained 1.80 g (8.56 mmol, 88% of the theoretical yield) of {(S)-2-methyl-1,4-dioxaspiro[4,5]-dec-2-yl}methanol, >99% pure by gas chromatography, >99% enantiomeric purity (ee), $[\alpha]_{365} = -20.1°$ (1% in $CHCl_3$) and $+20.9°$ (1% in $C_2H_5OH$).

[The likewise isolated ester fraction ({(S)-2-methyl-1,4-dioxaspiro[4,5]dec-2-yl}methyl butyrate) can be concentrated and hydrolyzed in alkaline solution to (R)-2-methyl-1,4-dioxaspiro[4,5]dec-2-yl}methanol].

EXAMPLE 8

Manufacture of
{(S)-2,2,4-trimethyl-1,3-dioxolan-4-yl}methanol
(asymmetric hydrolysis of
{(R,S)-2,2,4-trimethyl-1,3-dioxolan-4-yl}methyl butyrate, alternative method)

The procedure of Example 6 is repeated, but with the differences that 1.0 g (4.6 mmol) or 3.0 g (13.9 mmol) or 5.0 g (23.1 mmol) of the butyrate are used instead of 100 mg (462 μmol), and 1.0N sodium hydroxide solution is used as the titrating agent.

The respective details are set forth in Table 5 hereinafter:

TABLE 5

| Enzyme (amount used)*** | Amount of butyrate used | Percentage conversion/ reaction time | Percentage ee of the alcohol product |
| --- | --- | --- | --- |
| Lipase P-30 (600 U) | 1.0 g | 49.5/28 min. | 99.4 |
| Lipase P-30 (1800 U) | 3.0 g | 49.3/60 min. | 99.0 |
| Lipase P-30 (1800 U) | 5.0 g | 48.9/120 min. | 98.8 |
| Lipase PM [Palatase M 1000 L] (300 µl) | 1.0 g | 49.5/90 min. | 97.3 |
| Lipase LRD (1575 U) | 1.0 g | 49.5/132 min. | 94.4 |

***Amount in µl or U (amount of units used according to details declared by the supplier)

EXAMPLE 9

Manufacture of {(S)-2,2,4-trimethyl-1,3-dioxolan-4-yl}methanol (asymmetric hydrolysis of {(R,S)-2,2,4-trimethyl-1,3-dioxolan-4-yl}methyl butyrate 5.01 g (23.2 mmol) of {(R,S)-2,2,4-trimethyl-1,3-dioxolan-4-yl}methyl butyrate are emulsified in 25 ml of 0.1M sodium chloride solution and 1 ml of 0.1M sodium phosphate buffer at pH 7.5 (concentration of butyrate 16.1% w/v). The reaction is initiated by adding 50 mg of Lipase P-30. The pH value is held constant at 7.5 by stirring in 1.0N sodium hydroxide solution up to a 46.6 percent reaction conversion (reaction time 1 hour, addition of 10.8 ml of sodium hydroxide solution). Thereafter, the reaction is interrupted by the addition of 50 ml of methylene chloride. The reaction mixture is extracted twice with 50 ml of methylene chloride each time, the phase separation being accelerated by centrifugation for a short time, the combined organic phases are dried over anhydrous magnesium sulfate and the solvent is evaporated off at 12 mbar/30° C. This gives 4.07 g of an oil which is purified by chromatography over silica gel 60 (0.040–0.063 mm, 80 g) using n-hexane/ethyl acetate (2:1) as the eluent. In this manner there are obtained 1.33 g (9.11 mmol, 78.6% of the theoretical yield) of {(S)-2,2,4-trimethyl-1,3-dioxolan-4-yl}methanol, <99% pure according to gas chromatography, >99% enantiomeric purity (ee), $[\alpha]_{365} = -24.2°$ (1% in CHCl$_3$) and, respectively, $[\alpha]_{365} = +26.0°$ (0.5% in ethanol).

EXAMPLE 10

Production of {(R)-2-methyl-1,4-dioxaspiro[4,5]dec-2-yl}methyl tosylate

A solution of 1.67 g (7.94 mmol) of {(S)-2-methyl-1,4-dioxaspiro[4,5]dec-2-yl}methanol and 3 ml of triethylamine in 10 ml of methylene chloride is treated portionwise with 1.63 g (8.54 mmol) of tosyl chloride and the reaction mixture is left to stand for about 16 hours. The resulting brown mass is taken up in 100 ml of methylene chloride and the solution is washed twice with 100 ml of water each time. Subsequent evaporation of the organic phase gives 3.1 g of a brownish oil which is purified by chromatography over silica gel 60 (0.040–0.063 mm, 70 g) using methylene chloride as the eluent. There are obtained 2.33 g (6.84 mmol, 86% of the theoretical yield) of {(R)-2-methyl-1,4-dioxaspiro[4,5]dec-2-yl}methyl tosylate, 99% pure by gas chromatography, $[\alpha]_{365} = -29.0°$ (1% in CHCl$_3$).

EXAMPLE 11

Production of {(R)-2,2,4-trimethyl-1,3-dioxolan-4-yl}methyl tosylate

A solution of 1.15 g (7.86 mmol) of {(S)-2,2,4-trimethyl-1,3-dioxolan-4-yl}methanol and 3 ml of triethylamine in 25 ml of methylene chloride is treated portionwise with 1.90 g (9.96 mmol) of tosyl chloride and the reaction mixture is left to stand for about 16 hours. The reaction mixture is washed twice with 100 ml of water each time. Subsequent evaporation of the organic phase gives 3.04 g of a brownish oil which is purified by chromatography over silica gel 60 (0.040–0.063 mm, 80 g) using n-hexane/ethyl acetate (3:1) as the eluent; the first tosylate fractions obtained are again purified by chromatography using n-hexane/ethyl acetate (2:1) as the eluent. A total of 1.78 g (5.92 mmol, 75% of the theoretical yield) of {(R)-2,2,4-trimethyl-1,3-dioxolan-4-yl}methyl tosylate is obtained, 99% pure by gas chromatography, $[\alpha]_{365} = -37.1°$ (1% in CHCl$_3$).

EXAMPLE 12

Production of (R)-2,3-dihydroxy-2-methylpropyl tosylate 2.22 g (6.52 mmol) of {(R)-2-methyl-1,4-dioxaspiro[4,5]dec-2-yl}methyl tosylate are repeatedly evaporated from methanol in the presence of a catalytic amount of p-toluenesulfonic acid and the residue is finally purified by chromatography over silica gel 60 (0.040–0.063 mm, 55 g) using diethyl ether/methylene chloride (1:2) as the eluent. There are obtained 829 mg (3.18 mmol, 49% of the theoretical yield) of (R)-2,3-dihydroxy-2-methylpropyl tosylate, 98% pure by gas chromatography, $[\alpha]_{365} = -19.9°$ (1% in CHCl$_3$).

EXAMPLE 13

Production of (R)-2,3-dihydroxy-2-methylpropyl tosylate 1.42 g (4.74 mmol) of {(R)-2,2,4-trimethyl-1,3-dioxolan-4-yl}methyl tosylate are evaporated twice from 100 ml of methanol in the presence of a catalytic amount of p-toluenesulfonic acid at 16 mbar/40° C. and the residue is finally purified by chromatography over silica gel 60 (0.040–0.063 mm, 20 g) using methylene chloride/diethyl ether (1:1) as the eluent. There are obtained 907 mg (3.49 mmol, 74% of the theoretical yield) of (R)-2,3-dihydroxy-2-methylpropyl tosylate, 99% pure by gas chromatography, $[\alpha]_{365} = -19.0°$ (1% in CHCl$_3$).

EXAMPLE 14

Production of (R)-α-methyl-2-oxiranemethanol 816 mg (3.13 mmol) of (R)-2,3-dihydroxy-2-methylpropyl tosylate are dissolved in 50 ml of diethyl ether and the solution is treated portionwise with 1.08 g (9.68 mmol) of sodium tert.butylate. After stirring for 3 hours 100 µl (5.55 mmol) of water are added thereto and the mixture is stirred for a further 30 minutes. The resulting potassium tosylate is then filtered off and the filtrate is concentrated cautiously (readily volatile epoxide). The residue is purified by chromatography over silica gel 60 (0.040–0.063 mm, 20 g) using n-pentane/diethyl ether (in one direction gradually varying ratio of the two components) as the eluent. After careful concentration of the fraction there are obtained 72 mg of crude (R)-α-methyl-2-oxiranemethanol. The determination of the enantiomeric purity by capillary gas chromatography (chiral permethylated β-cyclodextrin phase) gives 99% ee of the (R)-isomer (reference comparison).

This means that the alcohol produced under the influence of the enzyme (see Examples 3–9 and 15) has the S-configuration, as in the case of the unreacted ester.

EXAMPLE 15

Manufacture of {(S)-2,2,4-trimethyl-1,3-dioxolan-4-yl}methanol (asymmetric hydrolysis of {(R,S)-2,2,4-trimethyl-1,3-dioxolan-4-yl}methyl butyrate using an immobilized enzyme)

(i) Partial purification of Lipase P-30: The purification is effected according to the method of M. Sugiura et al. [Biochim. Biophys. Acta 488, 353–358 (1977)]: 12.5 g of Lipase P-30 are taken up in 100 ml of sodium acetate buffer (10 mmol, pH 7.0) and the mixture is stirred at 4° C. for half an hour. The insoluble material is removed by centrifugation (43500 g, 20 min., 5° C.) and the solution remaining is diluted to 100 ml with a further amount of buffer, whereby the enzyme activity amounts to 2600 U/ml [for the measurement of this activity, 250 μl of tributyrin are emulsified in 25 ml of 0.1M sodium chloride solution and 1 ml of 0.1M sodium phosphate buffer (pH 7.0) and the reaction is initiated by the addition of the enzyme sample; the course of the reaction is monitored while maintaining a pH value of 7.0 by adding 0.1N sodium hydroxide solution]. 20.9 g of ammonium sulfate (35% saturation) are added to the solution within 30 minutes and the thus-formed suspension is stirred at 0° C. for a further 2.5 hours. Then the suspension is centrifuged as described above and the sediment (about 1 percent of the enzyme activity in the supernatant) is dissolved in a small amount of sodium phosphate buffer (50 mmol, pH 7.5) and dialyzed within 16 hours against 4×1 l of the same buffer at 4° C. [Spektra/Por, cut-off limit of the molecular weight 3500 (Spectrum Medical Industries, Los Angeles, Ca., USA)]. This gives 14.7 ml of a concentrated solution of Lipase P-30 (1.33·10⁴ U/ml; enzyme activity measured as described above).

(ii) Immobilization of lipase P-30: 500 μl of the lipase solution are diluted four times with the phosphate buffer described above and 500 mg of Eupergit C beadlets (Röhm, Weiterstadt, FRG) are added thereto. The suspension is then shaken gently at room temperature for 63 hours and the beadlets are subsequently filtered off, washed with 0.1M sodium chloride solution (about 0.1 percent of the enzyme activity in the filtrate) and dried at 16 mbar for 15 minutes. In this manner there are obtained 1.36 g of moist beadlets (234 U/g, this enzyme activity is measured as described above; stored at 4° C. for a few days).

(iii) Asymmetric hydrolysis: 10,0 g (46.2 mmol) of {(RS) 2,2,4 trimethyl-1,3-dioxolan-4-yl}methyl butyrate are emulsified in 185 ml of 0.1M sodium chloride solution and 5 ml of 0.1M sodium phosphate buffer (pH 7.5). After adjusting the pH value to 7.5 with 1.0N sodium hydroxide solution the reaction is initiated by the addition of 500 mg of moist Eupergit beadlets. The pH value is held constant at 7.5 by stirring in 1.0N sodium hydroxide solution. After the addition of a total of 22.2 ml (22.2 mmol; 48 percent reaction conversion after 6.9 hours) of titrating agent the enzyme beadlets are filtered off and washed five times with 10 ml of 0.1M sodium chloride solution each time. The filtrate is combined with the first washing solution and the combined aqueous phase is extracted four times with 200 ml of methylene chloride each time. The combined organic phases are then dried over anhydrous sodium sulfate and concentrated at 600 mbar/40° C. The residue is subjected to a column chromatography using silica gel 60 (0.040–0.063 mm) and n-hexane/ethyl acetate (2:1). In this manner there are obtained 3.02 g (20.7 mmol, 44.7% of the theoretical yield) of the title compound which by gas chromatography is found to be more than 95% pure and which has a percentage ee of more than 99%.

We claim:

1. A process for producing an S-enantiomer of the formula

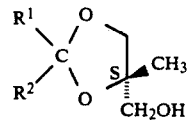

wherein R¹ and R² are independently methyl or ethyl or taken together form pentamethylene, comprising subjecting a racemic compound of the formula

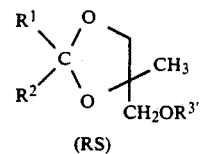

(RS)

wherein R¹ and R² are as above; and R³¹ is alkanoyl containing from 2 to 9 carbon atoms to enzymatic hydrolysis utilizing an enzyme selected from the group consisting of Lipase P-30, Lipase SAM, Lipase PM, Lipase LMM, Lipase LRD, Lipase D, Lipase LRA, Lipase CE, Lipase FAP and Lipase MAP, and thereafter recovering said S-enantiomer.

2. A process for isolating an S-enantiomer of the formula

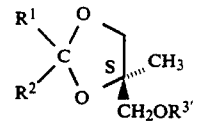

wherein R¹ and R² are independently methyl or ethyl or taken together form pentamethylene and R³' is alkanoyl containing from 2 to 9 carbon atoms, from the corresponding racemic ester, comprising subjecting said racemic ester of the formula:

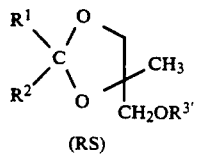

(RS)

wherein R¹, R² and R³' are as defined above, to enzymatic hydrolysis utilizing an enzyme, selected from the group consisting of Lipase P-30, Lipase SAM, Lipase PM, Lipase LMM, Lipase LRD, Lipase D, Lipase LRA, Lipase CE, Lipase FAP and Lipase MAP to produce an S-enantiomer of the formula:
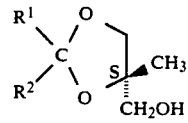
wherein $R^1$ and $R^2$ are as defined above,
stopping said enzymatic hydrolysis after about 50 percent of said racemic ester has been converted to the S-alcohol and isolating the S-ester from the mixture.
* * * * *